(12) United States Patent
Nilsson et al.

(10) Patent No.: US 6,763,588 B1
(45) Date of Patent: Jul. 20, 2004

(54) GAMMA RAY COLLIMATOR BUILD UP

(75) Inventors: Börje Nilsson, Uppsala (SE); Jürgen Arndt, Färentuna (SE)

(73) Assignee: Elekta AB, Stockholm (SE)

( * ) Notice: Subject to any disclaimer, the term of this patent is extended or adjusted under 35 U.S.C. 154(b) by 0 days.

(21) Appl. No.: 09/763,165
(22) PCT Filed: Sep. 7, 1999
(86) PCT No.: PCT/SE99/01553
§ 371 (c)(1),
(2), (4) Date: Mar. 20, 2001
(87) PCT Pub. No.: WO00/18538
PCT Pub. Date: Apr. 6, 2000

(30) Foreign Application Priority Data

Sep. 10, 1998 (SE) .............................. 9803065

(51) Int. Cl.⁷ ................................ B23P 15/16
(52) U.S. Cl. .................... 29/896.6; 29/463; 250/505.1; 378/147; 378/149
(58) Field of Search ............................. 29/896.6, 463, 29/432.1, 527.6, 557; 250/505.1; 378/147, 149; 72/333, 338, 340, 363

(56) References Cited

U.S. PATENT DOCUMENTS

| 2,169,937 | A | * | 8/1939 | Wempe |
| 3,457,619 | A | * | 7/1969 | Kydd |
| 4,450,706 | A | * | 5/1984 | Engelmohr |
| 4,465,540 | A | * | 8/1984 | Albert ...................... 156/252 |
| 4,780,898 | A |   | 10/1988 | Sundqvist |
| 5,212,718 | A |   | 5/1993 | Casanova |
| 5,448,611 | A |   | 9/1995 | Kerjean |
| 5,528,653 | A |   | 6/1996 | Song et al. |
| 5,803,671 | A | * | 9/1998 | Gray |

FOREIGN PATENT DOCUMENTS

DE       23 51 450      4/1975

OTHER PUBLICATIONS

Copy of International Search Report dated Jan. 24, 2000.
Copy of International Preliminary Examination Report dated Dec. 5, 2000.

* cited by examiner

Primary Examiner—I Cuda Rosenbaum
Assistant Examiner—Stephen Kenny
(74) Attorney, Agent, or Firm—Burns, Doane, Swecker & Mathis, L.L.P.

(57) ABSTRACT

A method of providing with precision a number of long and narrow through holes (11) in a body (1) made of a high-density material. The body (1) is made in the form of a number of partial bodies (2, 2', 2"), which are arranged close to each other and from the body (1). Each partial body (2, 2', 2") is defined by an outer surface (5), which is part of the outer surface of the entire body (1), an inner surface (6), which is part of the inner surface of the entire body (1), as well as a pair of boundary surfaces (7, 8), which extend from the outer surface (5) to the inner surface (6). Holes (11) are produced by machining at least one of the bounding surfaces (7, 8) adjacent partial bodies (2', 2"). Each hole (11) extends from the outer surface (5) to the inner surface (6) along said at least one boundary surface (7, 8). The thus machined partial bodies (2, 2', 2") are fixedly attached to each other.

20 Claims, 3 Drawing Sheets

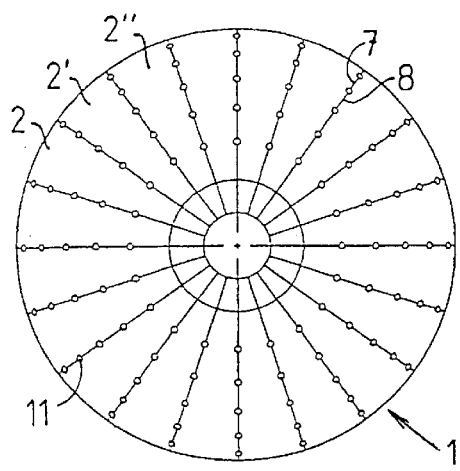
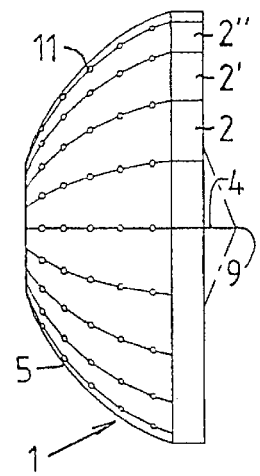
FIG 7　　　　　　　　　FIG 8
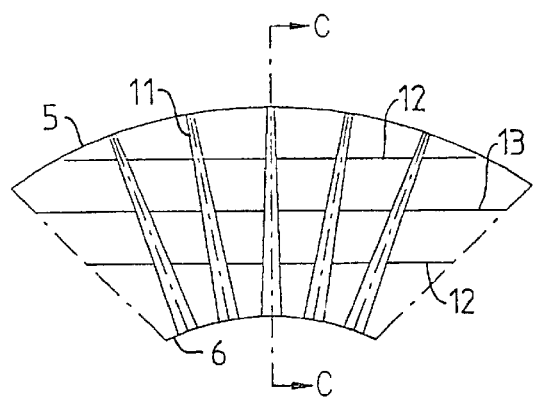
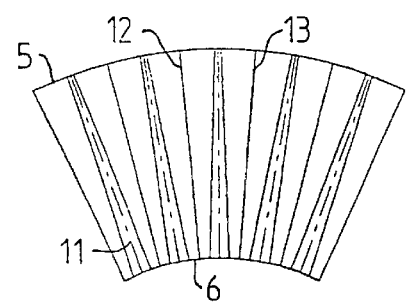
FIG 12　　　　　　　　　FIG 13
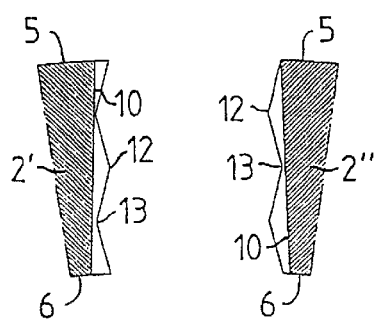
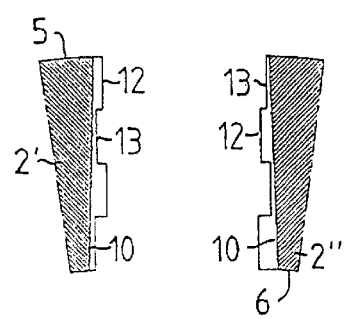
FIG 15　　　　　　　　　FIG 16

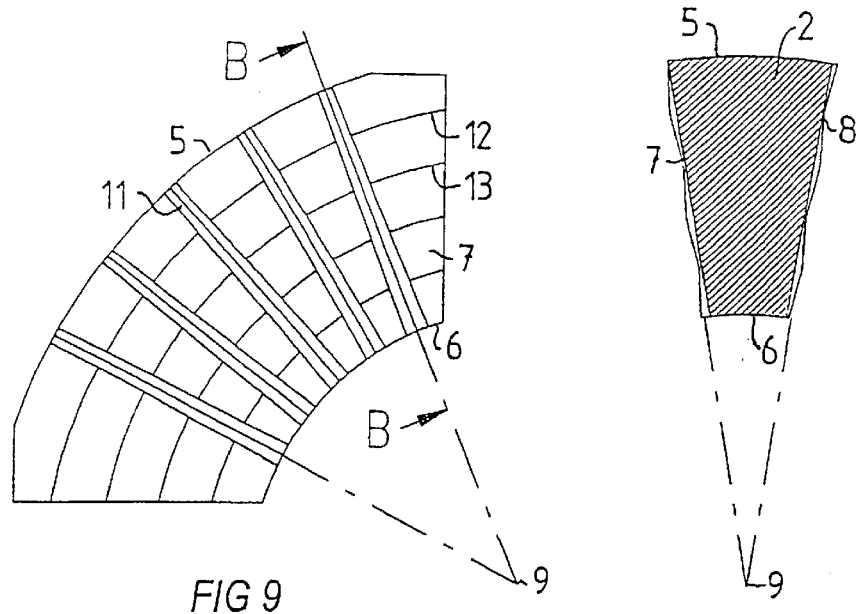
FIG 9
FIG 14
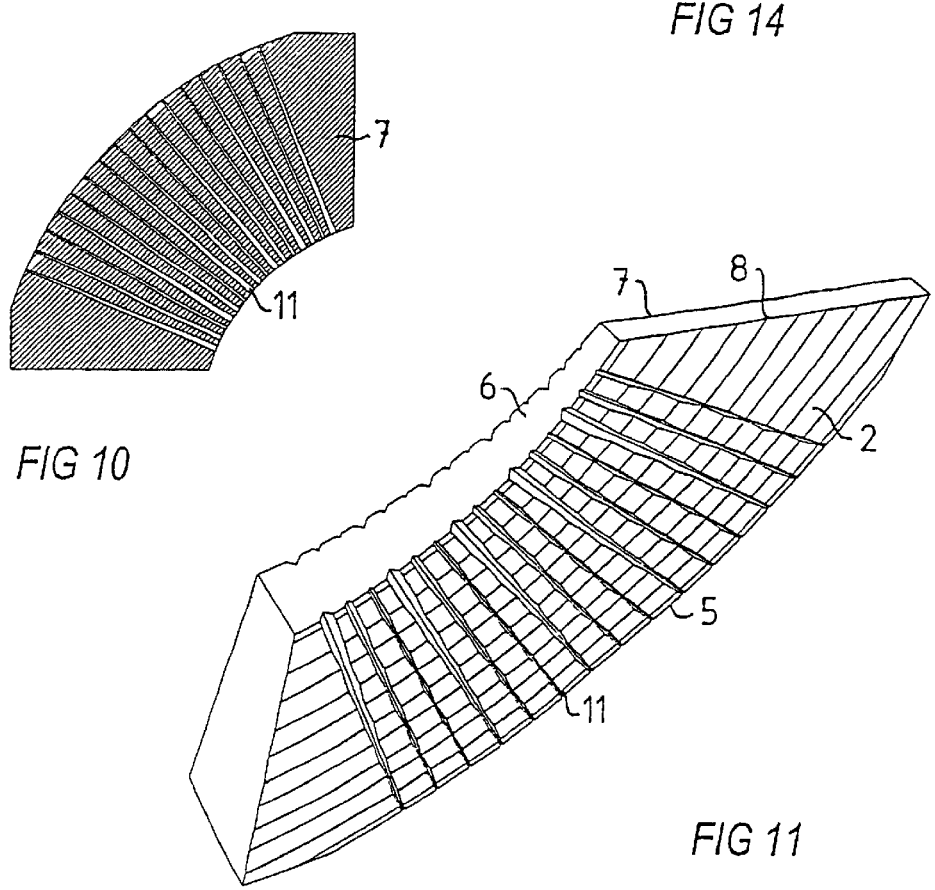
FIG 10
FIG 11

GAMMA RAY COLLIMATOR BUILD UP

The present invention relates to a method of providing with precision a number of long and narrow through holes in a body made of a high-density material.

Particularly, but not exclusively, the invention relates to the production of an integrated multichannel collimator for use in a device for radiation treatment of a human being or an animal, for instance, ELEKTA AB's gamma knife.

There are various technical suggestions on how to produce an integrated multichannel collimator and solve the problem of providing many hundreds of geometrically focussing long and narrow conical holes (length of about 200 mm) in a radiation-proof material, such as tungsten, uranium or lead. The narrow through holes or apertures preferably have different size or diameter. It is a technical challenge to produce the length and the small diameter of the conical holes as well as their great number and close spacing with geometric precision. In addition, the materials are difficult to work. In the case of, for instance, sintered tungsten, the largest single pieces which are commercially available weigh about 200 kg, and therefore a massive collimator of 1 tonne is an extremely large dimension challenging the sintering industry.

In the case of a collimator in one single piece, the only existing production alternatives are long-hole boring, spark machining and/or blanks with moulded holes. Boring as well as spark machining are time-consuming and expensive production methods and the required number of long conical holes with said dimensions and strict precision requirements constitute an economically nightmarish problem, which is further aggravated by the risk of rejection in the case of machining errors in an undivided collimator in one piece. Massive sintered tungsten has technical dimensional limitations in commercial production. Uranium has been moulded in single-piece weights of a few tonnes and is the most interesting choice of material from a technical/theoretical point of view, but relatively unknown in non-military production. The alternative production method of precision-moulding holed blanks is also very time-consuming and requires after-treatment, in particular as the long and narrow holes in the dome-shaped collimator build-up expand (converge) from the outside to the inside of the collimator.

An object of the present invention is to provide a method of producing with flexibility and great precision a number of long through holes with an optional, small diameter in a body made of a material which is difficult to machine.

Another object of the invention is to provide a comparatively inexpensive and functional method of producing long, narrow holes in a high-density material.

A further object of the invention is to provide a method which allows production of elongated holes with an optional section in the transverse as well as the longitudinal direction.

According to the invention, these objects are achieved with a method according to the introductory part, which is characterised in that the body is made in the form of a number of partial bodies, which are arranged close to each other and form said body, that each partial body is defined by an outer surface, which is part of the outer surface of the entire body, an inner surface, which is part of the inner surface of the entire body, as well as a pair of boundary surfaces, which extend from the outer surface to the inner surface, that said holes are produced by machining at least one of the boundary surfaces of adjacent partial bodies, each hole extending from the outer surface to the inner surface along said at least one boundary surface, and that the thus machined partial bodies are fixedly attached to each other.

Further developments of the invention will appear from the features stated in the dependent claims.

Preferred embodiments of the invention will now be illustrated as examples with reference to the accompanying drawings, in which FIG. 1 illustrates in axial section an embodiment of a collimator, which is produced by the method according to the invention;

FIG. 7 is a plan view illustrating on a reduced scale an alternative embodiment of a collimator, which is produced by the method according to the invention;

FIG. 8 is a side view of the collimator according to the alternative embodiment in FIG. 7;

Figure 1:
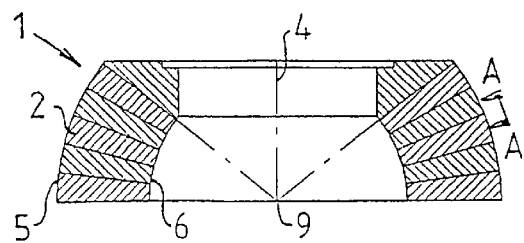

FIG. 9 schematically illustrates the positioning of the holes in the partial bodies and a possible design of the boundary surface of a partial body to prevent radiation leakage and to orient adjacent partial bodies, respectively;

FIG. 10 shows in more detail the design of the holes in the boundary surface of the partial body;

FIG. 11 is a perspective view of a partial body according to the embodiment in FIGS. 7–10;

FIG. 12 illustrates a possible design, which is an alternative to the one in FIG. 9, of the boundary surface of a partial body to prevent radiation leakage in the radial direction and to orient adjacent partial bodies;

FIG. 13 illustrates a further, alternative design of the boundary surface of a partial body to prevent radiation leakage between adjacent holes and to orient adjacent partial bodies;

FIG. 14 shows in more detail and in section along the line B—B in FIG. 9 the profiling of the boundary surface of the partial body;

FIG. 15 shows on a larger scale the elevations and depressions of the boundary surface of a pair of matching partial bodies in a separated state; and FIG. 16 is a view similar to that in FIG. 15 showing an alternative shape of the elevations and depressions of the boundary surface.

The method according to the invention may advantageously be applied in most situations, in which a number of long and narrow holes or channels are to be produced with precision in a body made of a hard material or of a high-density material or metal, such as tungsten, uranium, cobalt and iridium. Although the invention may be carried out on various geometrical shapes, it will be described below in connection with the production of a multichannel collimator for use in a device for radiation treatment of a human being or an animal, such as ELEKTA AB's gamma knife. Therefore, reference is made to Swedish patent 8602025-2 (U.S. Pat. No. 4,780,898, EP 7850124.7). The collimator is a body in the form of a substantially semispherical, thick shell or a dome. In the illustrated examples, the wall thickness is preferably about 200 mm and the number of the holes about 200. The diameter of the holes is 1–8 mm.

Corresponding details in the figures have been given the same reference numerals.

Figure 3:
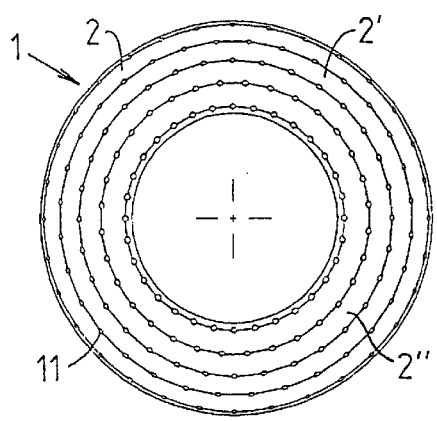
FIG. 3 is a plan view showing one of the partial bodies in FIG. 2.
Figure 2:
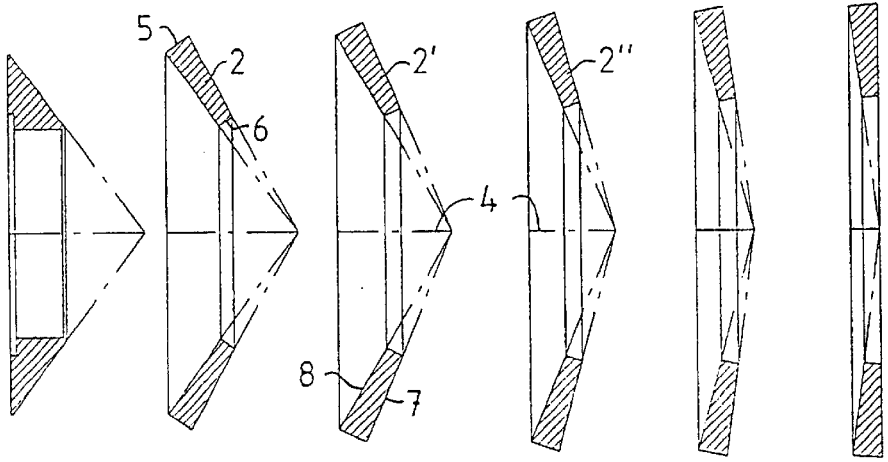
FIG. 2 is an exploded view in axial section, but turned through 90° relative to FIG. 1, and shows the partial bodies of the collimator.

With reference first to FIGS. 1–3, a first embodiment of a collimator is illustrated, which is produced by the method according to the invention.

As best shown in FIG. 1, the body 1 is produced in the form of a number of partial bodies 2, which are arranged close to each other and form the body 1. The partial bodies are fixedly attached to each other, for instance, by soldering and/or by means of a surrounding cover 3, which is indicated by broken lines in FIG. 4. Each partial body 2 is formed as an annular disc, which is rotationally symmetrical about the axis of symmetry 4 of the body 1, and each disc has a cone angle different from that of the other discs (see FIG. 2). Moreover, each partial body 2 is defined by an outer surface 5, which is part of the outer surface of the entire body 1, an inner surface 6, which is part of the inner surface of the entire body 1, as well as a pair of conical boundary surfaces 7 and 8, which extend from the outer surface 5 to the inner surface 6. The boundary surfaces 7 and 8, by means of which the partial bodies 2 abut against each other, are substantially directed towards the centre 9 of the dome (towards the centre of the sphere which has given its shape to the semispherical shell), cf. FIG. 1.

Figure 4:
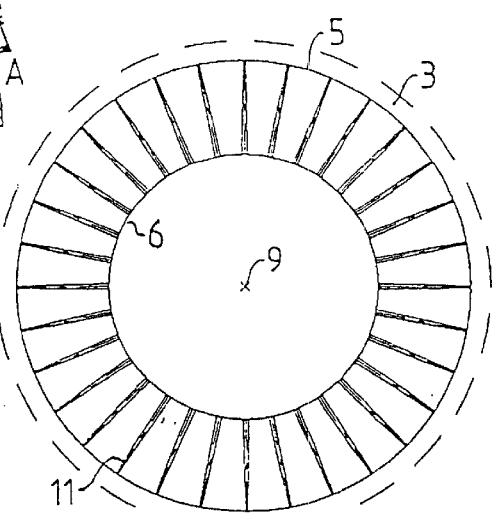
FIG. 4 is a plan view showing the assembled collimator according to the embodiment in FIGS. 1–3.
Figure 5:
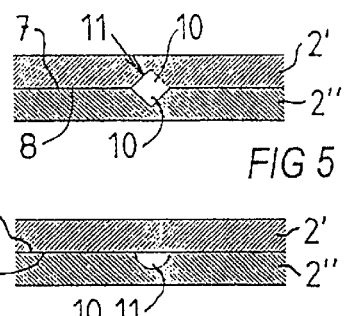
FIG. 5 shows the cross-sectional profile of a hole or an aperture on an enlarged scale along the line A—A in FIG. 1.
Figure 6:
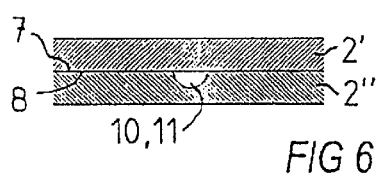
FIG. 6 is a view similar to the one in FIG. 5 showing an alternative cross-sectional profile.

A number of long and narrow through holes, beam channels, grooves or apertures 11, which extend from the outer surface 5 of the entire body 1 to its inner surface 6, have been produced by machining at least one of the boundary surfaces 7, 8 of adjacent partial bodies 2 (see FIG. 4). With reference to FIG. 5, one half or groove 10 of the beam channel 11 is produced in the boundary surface 7 of one of the partial bodies 2', whereas the other half or groove 10 of the channel is produced in the adjoining boundary surface 8 of the adjacent partial body 2", opposite to the first-mentioned half or groove so that they define the channel 11 together (cf. FIG. 3). Alternatively, a groove 10 is produced only in the boundary surface 8 of one of the partial bodies 2", the channel 11 being defined by the groove 10 in one of the boundary surfaces 8 and the opposite, unmachined portion in the boundary surface 7 of the adjacent partial body 2', as shown in FIG. 6.

The cross-sectional shape of the holes or the channels 11 can be designed as desired and have various profiles, for instance, circular, semicircular, oval, triangular, rectangular (see FIGS. 5 and 6), due to the fact that the grooves 10 are produced by machining the boundary surfaces 7, 8 of the partial bodies 2. As a result, also the longitudinal profile of the channels 11, i.e. from the outer surface 5 to the inner surface 6, may be designed as desired, for instance, of uniform thickness, continuously or stepwise tapered. For instance in FIG. 13, the channels 11 are shown with an increasing cross-section from the outer surface 5 towards the inner surface 6. By the method according to the invention, it is, of course, also possible to give the channels 11 a curved shape, if desired, and mutually different size (diameter).

The grooves 10 are thus made by machining the boundary surfaces 7 and/or 8 of the partial bodies 2. The machining may be carried out by milling, grinding, spark machining and/or planing. But it is also possible to produce the grooves by stamping or pressing, if the material of the body is sufficiently soft (e.g. made of lead). However, if the collimator is made of lead, the lead must be encapsulated (cf. the cover 3 in FIG. 4). Besides the above-mentioned materials, the collimator could also be made of iron. In this case, the grooves 10 in the partial bodies 2 are made larger, inserts of tungsten, uranium, cobalt, iridium or the like with beam channels machined as described above being arranged in a suitable manner in the grooves.

The rotationally symmetrical discs have the best possible geometrical shape for the intended production (cutting) and can easily be assembled with maintained geometrical precision. The production method is comparatively inexpensive and easy, and the partial bodies can be made of materials out of which it would have been difficult to produce an entire massive body (a collimator of prior-art design with bored holes).

In FIGS. 7–11, an alternative embodiment of the invention is illustrated. It differs from the above-described embodiment primarily in that the partial bodies 2, 2', 2" are not made as conical, annular discs but as "semisegments of an orange", that is the partial bodies 2 of the body 1 are formed as identical sector segments with their boundary surfaces 7 and 8 directed towards the axis of symmetry 4 of the body 2 (cf. in particular FIGS. 7 and 11). The grooves 10 of the holes 11, which also in this case are machined in the boundary surfaces 7 and/or 8 of the partial bodies 2, 2', 2", are arranged in a common plane for each boundary surface 7, 8, each such plane extending through said axis of symmetry 4 (cf. FIG. 7). As to the rest, the holes 11 are produced and formed as stated in connection with the first-mentioned embodiment. Compared to the disc model, "the orange segment model" comprises a greater number of partial bodies having dimensions which are more advantageous in terms of production-technique, and has the same accessibility to the open channels.

The principle and basis of the collimator is thus to (systematically) divide the body of the collimator into a number of selected section planes, which all cut the focal point of the collimator, and to arrange a number of open channels in the boundary surfaces of the partial bodies, said channels being oriented towards the same focal point. When assembled, the partial bodies together form a closed collimator having focussed closed channels or grooves.

The boundary surfaces may be identical with the focal planes or formed with small geometrical deviations from the focal planes to extinguish any radiation leaking in the lateral direction between the boundary surfaces (by inserting different seals). By small deviations is meant (varying) distances to the focal planes in the order of the cross-section of the channels of the collimator at the (varying) focal distance in question.

There is a risk that the division of the collimator results in undesired leakage radiation from the separation or boundary surfaces 7, 8 which must be taken into consideration. Geometrically, this risk can be eliminated by means of pleated sector elements. The pleats in the section plane are preferably made by lathe turning.

Different designs of leakage seals are schematically shown in FIGS. 9 and 11–16. As appears from FIGS. 9 and 11, the leakage sealing has been presented in connection with the "orange segment model", but a man skilled in the art will realise that it may also be applied to the "disc model". The boundary surfaces 7 and 8 have a structure with circular, concentric pleats, comprising elevations 12 alternating with depressions 13 in the radial direction, since the elevations 12 and the depressions 13 are arranged as concentric circles about the axis of symmetry 4 of the body 1. All the elevations 12 of a partial body (e.g. 2') may thus be closely fit into the corresponding depressions 13 of the adjacent partial body (e.g. 2") and vice versa (cf. FIGS. 15 and 16). This also gives the advantage that the partial bodies 2 are positioned correctly and firmly in relation to each other when assembling the entire body 1. In addition to the pleated structure, the boundary surfaces 7, 8 may also be corrugated, labyrinth-shaped, stepped or the like and comprise sealingly interacting elevations and depressions, respectively.

As seen in FIG. 12, the pleats, instead of being formed as concentric circles, may thus be made, for instance, as straight, parallel lines.

In order to prevent radiation leakage between adjacent channels 11, the pleats are advantageously radially arranged, that is each pleat extends from the outer surface 5 of the associated partial body 2 to its inner surface 6, substantially oriented towards the axis of symmetry 4 of the partial body. This is illustrated in FIG. 13.

Examples of the profile of the pleated structure or the boundary surface 7, 8 are schematically shown in FIGS. 15 and 16, which show sections along the line C—C through a channel 11 in FIG. 12. In FIG. 15, the boundary surfaces are formed with triangular pleats. Each elevation 12 of a partial body 2' is intended to be fit into a matching depression 13 of the adjacent partial body 2" and vice versa. Instead of forming the elevations and the depressions, respectively, to be pointed, they can be rectangular, in which case the plane surface of the elevation 12 of a partial body 2', when assembling the collimator according to the invention, will abut against the plane surface of the matching depression 13 of an adjacent partial body 2" and vice versa, as shown in FIG. 16.

Moreover, it is possible to obtain the radiation-sealing function in even boundary surfaces by means of insert elements, for instance, annular elements which are fit into opposite grooves in the boundary surfaces of adjacent partial bodies (not shown). Pressure-sintering is also a possible technique of achieving radiation tightness.

In the above description, a plurality of materials have been stated, of which the collimator may advantageously be made. If use is made of, for instance, lead or uranium, the final product should be encapsulated in a rust and corrosive resisting material because of its toxicity and for radiation safety reasons.

The invention is not limited to that described above and shown in the drawings, and may be modified within the scope of the appended claims.

What is claimed is:

1. A method of providing at least one long and narrow through hole in a collimator body made of a high-density material, the body being made from a plurality of partial bodies that are arranged relative to each other to form the body, each partial body being defined by an outer surface of the partial body which is part of an outer surface of the body, an inner surface of the partial body which is part of an inner surface of the body, and a pair of boundary surfaces that extend from the outer surface of the partial body to the inner surface of the partial body, comprising:

for at least a first hole of the at least one hole, machining a groove in a first boundary surface of a first partial body, the groove extending from the outer surface of the first partial body to the inner surface of the first partial body along the first boundary surface; and fixedly attaching a first boundary surface of a second partial body to the first boundary surface of first partial body such that the first hole is at least partially defined by the groove.

2. A method as claimed in claim 1, comprising, for at least the first hole, machining a second groove in the first boundary surface of the second partial body and fixedly attaching the first boundary surface of the second partial body to the first boundary surface of the first boundary surface such that the groove and the second groove together define the first hole.

3. A method as claimed in claim 1, wherein the first hole is defined by the groove in the first boundary surface of the first partial body and by the first boundary surface of the second partial body.

4. A method as claimed in claim 2, comprising machining a cross-sectional shape of each of the first and second grooves to be at least one of semicircular, triangular, and rectangular.

5. A method as claimed in claim 4, comprising machining the first and second grooves so that a cross-sectional area of the first hole decreases from the inner surface of the body towards the outer surface of the body.

6. A method as claimed in claim 1, comprising forming the first boundary surface of the first partial body and the first boundary surface of the second partial body to have a profile having elevations and depressions that mate with depressions and elevations of the second partial body and the first partial body, respectively, when the first boundary surface of the first partial body is fixedly attached to the first boundary surface of the second partial body.

7. A method as claimed in claim 1, wherein the body is in a form of a dome, comprising forming a plurality of partial bodies as annular discs.

8. A method as claimed in claim 1, wherein the body is in a form of a dome, comprising forming a plurality of partial bodies as sector segments each having boundary surfaces directed towards an axis of symmetry of the dome.

9. A method as claimed in claim 1, comprising fixedly attaching the first and second partial bodies by at least one of soldering and providing a surrounding cover.

10. A method as claimed in claim 3, comprising machining a cross-sectional shape of each of the first and second grooves to be at least one of semi-circular, triangular, and rectangular.

11. A method as claimed in claim 2, comprising forming the first boundary surface of the first partial body and the first boundary surface of the second partial body to have a profile having elevations and depressions that mate with depressions and elevations of the second partial body and the first partial body, respectively, when the first boundary surface of the first partial body is fixedly attached to the first boundary surface of the second partial body.

12. A method as claimed in claim 3, comprising forming the first boundary surface of the first partial body and the first boundary surface of the second partial body to have a profile having elevations and depressions that mate with depressions and elevations of the second partial body and the first partial body, respectively, when the first boundary surface of the first partial body is fixedly attached to the first boundary surface of the second partial body.

13. A method as claimed in claim 4, comprising forming the first boundary surface of the first partial body and the first boundary surface of the second partial body to have a profile having elevations and depressions that mate with depressions and elevations of the second partial body and the first partial body, respectively, when the first boundary surface of the first partial body is fixedly attached to the first boundary surface of the second partial body.

14. A method as claimed in claim 5, comprising forming the first boundary surface of the first partial body and the first boundary surface of the second partial body to have a profile having elevations and depressions that mate with depressions and elevations of the second partial body and the first partial body, respectively, when the first boundary surface of the first partial body is fixedly attached to the first boundary surface of the second partial body.

15. A method as claimed in claim 2, wherein the body is in a form of a dome, comprising forming a plurality of partial bodies as annular discs.

16. A method as claimed in claim 3, wherein the body is in a form of a dome, comprising forming a plurality of partial bodies as annular discs.

17. A method as claimed in claim 2, wherein the body is in a form of a dome, comprising forming a plurality of partial bodies as sector segments each having boundary surfaces directed towards an axis of symmetry of the dome.

18. A method as claimed in claim 3, wherein the body is in a form of a dome, comprising forming a plurality of partial bodies as sector segments each having boundary surfaces directed towards an axis of symmetry of the dome.

19. A method as claimed in claim 2, comprising fixedly attaching the first and second partial bodies by at least one of soldering and providing a surrounding cover.

20. A method as claimed in claim 1, wherein machining is one of milling and grinding.

* * * * *